US009485473B2

(12) United States Patent
Allen et al.

(10) Patent No.: US 9,485,473 B2
(45) Date of Patent: Nov. 1, 2016

(54) METHOD AND SYSTEM FOR DETERMINING QUALITY OF TUBES

(71) Applicant: ALSTOM Technology Ltd, Baden (CH)

(72) Inventors: Matthew David Allen, Enfield, CT (US); Allan Gunn Ferry, Windsor, CT (US); Ronald Francis Konopacki, Suffield, CT (US); Robert F. Crocker, East Granby, CT (US)

(73) Assignee: ALSTOM TECHNOLOGY LTD, Baden (CH)

( * ) Notice: Subject to any disclaimer, the term of this patent is extended or adjusted under 35 U.S.C. 154(b) by 357 days.

(21) Appl. No.: 13/968,887

(22) Filed: Aug. 16, 2013

(65) Prior Publication Data

US 2014/0071266 A1 Mar. 13, 2014

Related U.S. Application Data

(60) Provisional application No. 61/700,750, filed on Sep. 13, 2012, provisional application No. 61/700,788, filed on Sep. 13, 2012.

(51) Int. Cl.
*H04N 7/00* (2011.01)
*H04N 7/18* (2006.01)
*G01N 21/88* (2006.01)
*G01N 21/952* (2006.01)

(52) U.S. Cl.
CPC ............ *H04N 7/18* (2013.01); *G01N 21/8851* (2013.01); *G01N 21/952* (2013.01)

(58) Field of Classification Search
CPC .............................. H04N 7/18; G01N 21/952
USPC .......................................................... 348/84
See application file for complete search history.

(56) References Cited

U.S. PATENT DOCUMENTS 4,255,762 A    3/1981  Takeyasu et al.
5,099,115 A *  3/1992  Cruickshank ........ G03B 37/005
                                                          250/236

(Continued)

FOREIGN PATENT DOCUMENTS

CA      2 779 873       6/2011
DE   10 2007 052033     5/2009

(Continued)

OTHER PUBLICATIONS

Unofficial English translation of JP Office Action issued in connection with corresponding JP Application No. 2013-190822 on Aug. 16, 2016.

*Primary Examiner* — Jeffery Williams
(74) *Attorney, Agent, or Firm* — GE Global Patent Operation; Stephen G. Midgley

(57) ABSTRACT

Disclosed herein is a system having an optically transparent substrate having a first side and a second side that are opposed to each other, a microprocessor, a database, a camera disposed upon the first side of the optically transparent substrate and a source of illumination. The source of illumination is disposed in a ring around the camera on the first side and is operative to illuminate the object disposed on the second side of the optically transparent substrate. Further the camera is in operative communication with the microprocessor and the database. The camera is operative to capture an image of an object disposed upon the second side of the optically transparent substrate. The microprocessor is operative to calculate dimensions and geometry of the object from the image and facilitate acceptance or rejection of the object based upon a standard, a parameter or a calibration chart.

16 Claims, 3 Drawing Sheets

(56) References Cited

U.S. PATENT DOCUMENTS

| | | | |
|---|---|---|---|
| 5,517,033 A * | 5/1996 | Krivanek | H01J 37/224 250/397 |
| 5,793,468 A | 8/1998 | Shalon et al. | |
| 5,864,601 A * | 1/1999 | Cattorini | G01N 23/04 378/54 |
| 2004/0031337 A1 * | 2/2004 | Masaniello | F17D 5/02 73/865.8 |
| 2004/0128111 A1 * | 7/2004 | Lang | F22B 35/18 702/188 |
| 2004/0245338 A1 * | 12/2004 | Poloniewicz | G06K 7/10653 235/454 |
| 2006/0050092 A1 | 3/2006 | Bondurant et al. | |
| 2008/0087065 A1 * | 4/2008 | Hainzinger | B21D 7/024 72/31.05 |
| 2010/0039640 A1 | 2/2010 | Colle | |
| 2011/0279828 A1 * | 11/2011 | Matsumoto | F22B 37/005 356/630 |

FOREIGN PATENT DOCUMENTS

| | | | |
|---|---|---|---|
| EP | 1 707 918 | 10/2006 | |
| EP | 2 295 931 | 3/2011 | |
| JP | S54153763 A | 12/1979 | |
| JP | S61 50005 A | 3/1986 | |
| JP | H02275305 A | 9/1990 | |
| JP | H04 346011 A | 12/1992 | |
| JP | 05-240619 A | 9/1993 | |
| JP | H09-72726 | 3/1997 | |
| JP | H10-38531 | 2/1998 | |
| JP | H1038531 A * | 2/1998 | G01B 11/24 |
| JP | 11295028 A | 10/1999 | |
| JP | 2000-009436 | 1/2000 | |
| JP | 2001 000207 A | 1/2001 | |
| JP | 2001141419 A | 5/2001 | |
| JP | 2002-230523 | 8/2002 | |
| JP | 2005-134294 A | 5/2005 | |
| JP | 2007-057344 | 3/2007 | |
| JP | 2008-261679 | 10/2008 | |
| JP | 2009-115526 A | 5/2009 | |
| JP | 2010002232 A * | 1/2010 | G01B 11/24 |
| JP | 2010-101863 | 5/2010 | |
| JP | WO 2011074261 A1 * | 6/2011 | B21C 37/06 |
| JP | 2012-154858 | 8/2012 | |
| WO | 2011/074261 A | 6/2011 | |
| WO | 2011/138524 | 11/2011 | |

* cited by examiner

METHOD AND SYSTEM FOR DETERMINING QUALITY OF TUBES

CROSS-REFERENCE TO RELATED APPLICATION

This application claims priority to U.S. Provisional Application No. 61/700,750 filed Sep. 13, 2012, related U.S. Non-Provisional application (Ser. No. 13/968,874) filed concurrently herewith titled, "METHOD AND SYSTEM FOR DETERMINING QUALITY OF TUBES", and to U.S. Provisional Application No. 61/700,788 filed Sep. 13, 2012 the disclosures of which are each hereby incorporated in their entirety.

TECHNICAL FIELD

This disclosure relates to a method and to a system for determining the quality of tubes. In particular, this disclosure relates to a system that enables an automated method of determining the quality of linear tubes and bent tubes used in boilers.

BACKGROUND

Boiler tube manufacturing uses a variety of different sized steel alloy tubes. The tubes are bent during the manufacturing process, often by drawing the tube around a round die having the desired bend diameter. Metal in the tube walls are displaced during the bending process. In addition, the inner circumference and the outer circumference may lose their roundness (circularity) during the bending process, resulting in the loss of roundness for sections of the tube.

Both, the U.S. American Society of Manufacturing Engineers (ASME) boiler code and the European EN boiler code regulations mandate the inspection of tube bends for several properties such as the minimum tube wall thickness, maximum tube wall thickness, flow area through the tube, ovality (out-of roundness) and flat spots. The inspection as per the ASME and the EN regulations mandate that the tube bend be first sectioned into several pieces to expose several cross-sections of the tube. The measurements of these cross-sections are taken with mechanical measuring equipment such as a vernier caliper or a micrometer. In some cases, an image of the cross-section of the tube is stamped onto a piece of paper (using ink) and the measurements are made on the image.

Both sets of boiler regulations (ASME and EN) specify calculations that must be performed based on the measurements, with accepted criteria for each calculated value. Typically, an inspection report is created after taking the cross-sectional measurements of the tube and performing the desired calculations. The inspection report details whether a particular bend sample failed or passed. This complete process may take several days if performed by an inspection laboratory.

In addition, the method of mechanical measurement is subject to human error and equipment error that occurs with extensive equipment use. It is therefore desirable to use a method that is quicker and that is less error prone.

SUMMARY

Disclosed herein is a system comprising an optically transparent substrate having a first side and a second side that are opposed to each other; a microprocessor; a database; a camera disposed on the first side of the optically transparent substrate; and a source of illumination; the source of illumination being disposed in a ring around the camera on the first side and being operative to illuminate the object disposed on the second side of the optically transparent substrate; where the camera is in operative communication with the microprocessor and the database; where the camera is operative to capture an image of an object disposed upon the second side of the optically transparent substrate; where the microprocessor is operative to calculate dimensions and geometry of the object from the image and facilitate acceptance or rejection of the object based upon a parameter.

Disclosed herein too is a method comprising disposing a cross-sectional area of a linear tube on a first side of an optically transparent substrate; where the cross-sectional area is taken perpendicular to an axis that passes through a center of mass of the cross-sectional area; imaging the cross-sectional area to obtain an image; transmitting the image to a microprocessor; segmenting the image into a plurality of segments; measuring an inner diameter and an outer diameter for each segment of the plurality of segments; and determining an inner diameter, an outer diameter, a center of mass, a wall thickness, an out of roundness and a flow area for the tube.

BRIEF DESCRIPTION OF THE DRAWINGS OF THE DISCLOSURE

DETAILED DESCRIPTION

Disclosed herein is a system for measuring the various characteristics (dimensions and geometry) of a tube. The tube can be straight (without any bends) or bent. In an exemplary embodiment, the system is used for measuring the dimensions and geometry of a bent tube. The system comprises an optically transparent substrate, a source of illumination, a camera, a microprocessor and a database. In one embodiment, the camera contains the microprocessor and thus communicates with the database. The database may be part of a computer and will hereinafter be referred to as a computer database.

Disclosed herein too is a method that quickly and accurately inspects multiple tube cross-sections cut from a tube, performs the desired measurements on each cross-section and calculates the desired values, such as the values prescribed by ASME B31.1-2010 and EN 2 952-5. The method also includes generating an inspection report for each tube and saves the inspection date to a database. The method can be used on linear tubes or bent tubes. The method also involves storing, processing and transmitting the data in the computer database.

The method has significant advantages over other previously used methods that include the automatic collection of measurements by personnel who do not need any specific training. The measurement of tube geometry uses more measurement points and provides a more accurate and repeatable result than measurements made by hand with a vernier caliper and micrometer. Automatic transfer of the measured data from the camera to the microprocessor and to the database prevents transcription errors. Automatic performance of complex mathematical calculations can be conducted by shop personnel with little or no training. The method results in a reduction in hand calculation errors when compared with other traditional methods. Inspection reports can be obtained in several languages. Native speakers of different human languages can use the system and method in their preferred language. Inspection results can be obtained in under an hour (this includes tube preparation time such as cutting sections and polishing the cut ends to remove sharp edges).

Figure 1:
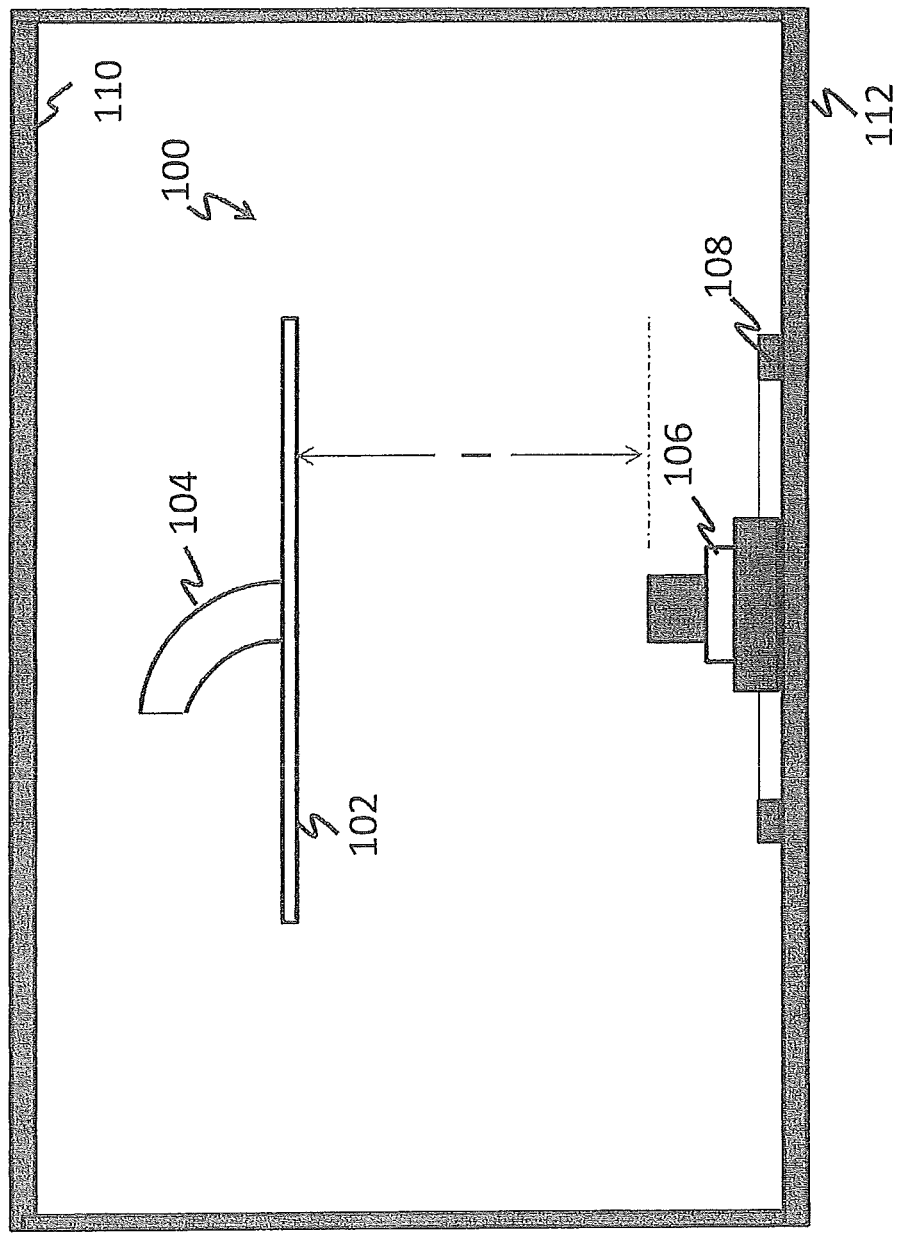
FIG. 1 is a depiction of an exemplary system that is used for measuring the dimensions and geometry of a tube.

FIG. 1 depicts a system 100 that is used for measuring the dimensional and geometric properties of a tube. The system 100 comprises an optically transparent substrate 102 upon which is disposed a section of the bent tube 104. The transparent substrate 102 has a first side and a second side, where the second side is opposed to the first side. While the figure depicts a bent tube, it is to be noted that the tube does not have to be bent, but can be linear. The section of bent tube 104 is derived from a bent tube that has been cut into a number of sections for purposes of examination. A cross-section of the bent tube 104 directly contacts a surface (on the first side) of the optically transparent substrate 102. The bent tube is not part of the system 100, but is one whose properties are to be measured. A camera 106 is disposed on the second side of the optically transparent substrate 102 that is opposed to the first side upon which the bent tube 104 is disposed. The camera may or may not contact the optically transparent substrate 102. Disposed substantially concentrically around the camera 106 is a source of illumination 108. The source of illumination 108 optically illuminates the cross-section of the bent tube 104. An opaque sheet 110 is optionally disposed over the top of the system 100 to prevent any external light from causing distortions in the image collected by the camera 106. In one embodiment, the entire system 100 may be enclosed in an opaque case 112 to prevent external light from distorting (or otherwise causing optical aberrations) the image collected by the camera 106. The opaque case has an inner surface that is not reflective and has an opening through which the tube may be inserted for imaging and then removed.

Figure 3:
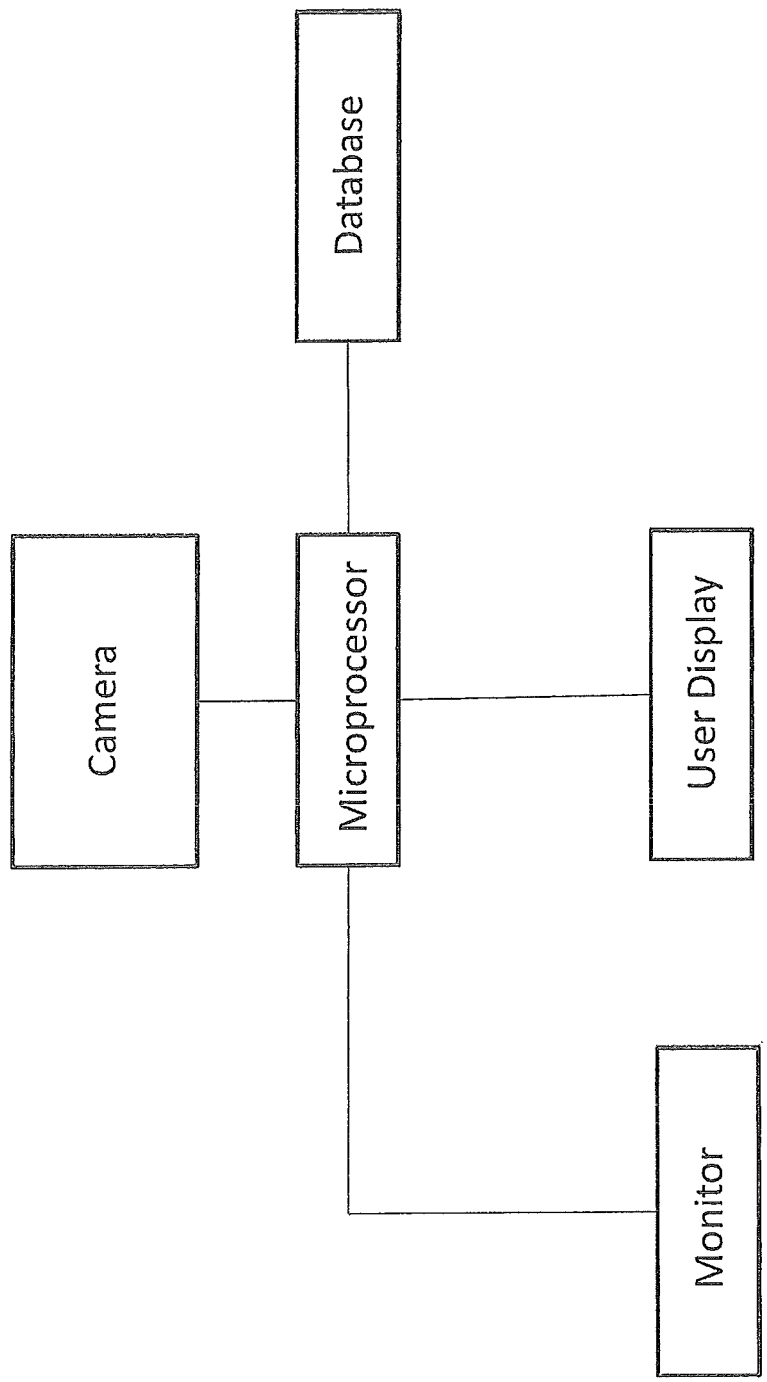
FIG. 3 depicts an exemplary system for processing and storing data obtained from the camera.

The camera 106 may be in operative communication with the microprocessor and the computer database. A small touch screen monitor (camera screen) permits triggering inspections and viewing camera image data. The FIG. 3 is a depiction of the communication between the camera of the system 100, a microprocessor, a monitor, a database and a user display. The camera is in operative communication with the microprocessor, which is in operative communication with a monitor, a user display and the database. Samples that are disposed upon the optically transparent substrate have their images disposed on the user display. The user display can be used to annotate the image and to locate the tube properly on the optically transparent substrate prior to taking an image. The microprocessor can be used to compute the tube dimensions based upon the image. The data along with calculations can then be stored on the database. Additional details of the user interface are provided below. In one embodiment, the operative communication includes electrical communication. A panel computer with a large touch screen monitor (main screen) provides annotation, analysis, quality record generation and storage. Network connectivity provides external access to data and records.

The electrical communication between the microprocessor and the database can include electrical hard wiring, wireless communication, or a combination thereof. The microprocessor and the computer database can be in communication with the internet. In an exemplary embodiment, the camera 106 is a digital camera with an image processing capability (i.e., it contains the microprocessor, which comprises an image processing library that is operative to process data obtained from images recorded by the camera). An exemplary camera may be purchased from the Cognex company.

The image processing library within the camera is used for the image acquisition, camera communication, cross sectional thickness detection, center of mass calculation, and cross-sectional area (fluid flow area) calculation. In addition, functions of the image processing library are used, through custom code, to perform inner diameter and outer diameter measurements. Given the center of the tube and the multiple (e.g., 72) inner diameter and outer diameter measurements, additional custom software calculates out of roundness, wall thickness, flatness; and statistics (minima, maxima, averages) for inner diameter, outer diameter, and wall thickness.

The image processing library is therefore used to determine properties of the tube such as, for example, the center of mass of the tube, the inner diameter of the tube, the outer diameter of the tube, the out of roundness of the tube, the wall thickness, the area of flow, and the presence of flat spots on the inner diameter of the tube. The database stores data obtained from the microprocessor and can use the data to calculate the overall characteristics of the bend, such as the radius of the bend, the flow area across the bend, and the like. In one embodiment, the system 100 can comprise a monitor for controlling the camera and for displaying an image of the tube cross-sectional area and other results. The monitor is in electrical communication with a computer that contains a data base for overall system control, annotations, data storage, reporting and network access, The camera 106 is used to image the cross-section of the linear tube or bent tube that is disposed upon the substrate 102. The distance "1" from the camera to the surface of the substrate that contacts the cross-section of the bent tube is known and is used in measuring the dimensions of the tube. The camera 106 is provided with a means to maintain the camera at a fixed distance "1" from the surface of the optically transparent substrate. This enables that the different measurements are not made a different magnifications.

The camera 106 is used to take a single image or a plurality of images of the cross-section of the tube and transmits these images to the microprocessor. In one embodiment, the camera 106 is used to take 1 to 12 images of each cross-sectional area of the tube. In an exemplary embodiment, the camera 106 is used to take a single image of the cross-section of the tube. This image is then processed in the microprocessor, i.e., it is divided into sections and each section has its inner diameter and outer diameter measured, following which the properties of the tube (e.g., the center of mass, the wall thickness, the fluid flow area, and the like) can be measured.

It is desirable for the optically transparent substrate 102 upon which the tube 104 is mounted to have a transparency of greater than 75%, specifically greater than 85% and more specifically greater than 95%, based on the intensity of light that is incident upon the substrate. In one embodiment, the optically transparent substrate can transmit at least 75%, specifically at least 85% and more specifically at least 95% of the light that is incident upon it. The optically transparent substrate is generally about 6 inches×6 inches in size, is scratch resistant and can be manufactured from an optically transparent material such as quartz, silica, alumina, titania, optically transparent polymers, and the like. Examples of optically transparent polymers that can be used are polystyrene, polycarbonate, polymethylmethacrylate, polycarbonate, polyester, polyetherimide, or the like, or a combination comprising at least one of the foregoing polymers. In one embodiment, a scratch resistant coating may be disposed upon the substrate. The optically transparent substrate may be in the form of a flexible film or in the form of a solid rigid panel. In one embodiment, the optically transparent substrate 102 may have grid lines disposed thereon to facilitate positioning of the tubes.

As noted above, the system 100 can be optionally housed in an opaque case 112 or covered by only an opaque sheet 110. The opaque case 112 or the opaque sheet 110 functions to prevent external light from impinging on the camera 106 and distorting the collected image. The opaque case may be manufactured from wood, textile, metal, ceramics or polymers so long as the material prevents light from entering the camera 106 and does not extensively reflect light from the source of illumination 108.

The source of illumination 108 is preferably concentrically distributed around the camera 106. The source of illumination 108 can comprise a fluorescent source of illumination or can comprise light emitting diodes (LED) that are arranged in the form of a ring around the camera 106. It is desirable to use a point source of illumination as the source of illumination to prevent image distortion because of multiple reflections. The point source of illumination is arranged in the form of a ring around the camera. It is desirable to have the ring be concentrically arranged around the lens of the camera. In an exemplary embodiment, the point a source of illumination is a light emitting diode (LED). In one embodiment, the source of illumination 108 (e.g., the light ring) used to illuminate the tube cross-sectional area for the camera, is actually positioned closer to the optically transparent substrate 102 than the camera. This provides illumination of the cross-sectional area itself, while minimizing illumination of the inner surfaces of the tube.

Figure 2:
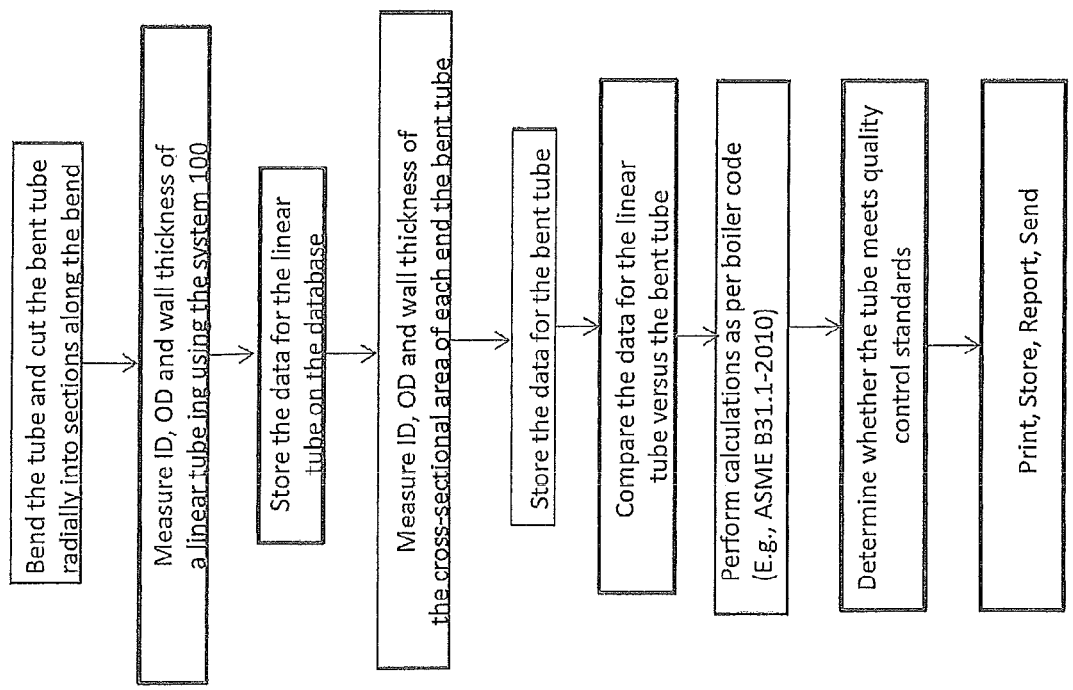
FIG. 2 depicts an exemplary method for measuring the dimensions and geometry of a bent tube.

The FIG. 2 represents an exemplary method of measuring the properties of a linear or a bent tube. In one embodiment, in one method of using the system, a cross-section of a tube is disposed upon a surface of the optically transparent substrate 102 and contacts it directly. A linear tube is first cut and a cross-section of the cut linear tube (i.e., an unbent tube) is disposed upon the substrate 102 to determine its inner diameter and outer diameter. The camera 106 is operated to obtain an image of the cross-sectional area of the cut tube and this image is then used to compute the inner diameter, the outer diameter, wall thickness, the out of roundness, the length and area of any flat spots on the inner or outer circumference, the center of mass, and the like. These measurements and the computations resulting from these dimensions and geometrical features is then stored on the computer database. The protocol (i.e., image processing) for obtaining these dimensions and geometrical features is detailed below in brief. If a series of unbent tubes are to be measured, these features can be calculated for each tube and stored on the computer database. This data can be used to compare with the data obtained on other linear tubes or even with a bent tube. In one embodiment, it is used as a baseline for a comparison with bent tube sections.

When the dimensions and properties of a bent tube are desired, the tube is first bent to the desired dimensions. It is to be noted that although the tube being assessed is bent, the sections analyzed are not all bent. The dimensioning system is used to capture and measure dimensional data from both bent and unbent cross sections, within and around the bend. It also dimensions standard (nominal, unbent) sections, for reference during calculations and assessment.

Bent portions of the tube 104 are cut into a plurality of sections and each section is disposed upon the transparent substrate 102. In one embodiment, the bent tube is cut into 2 to 10 sections, specifically 3 to 7 sections, and the opposing ends of each section is mounted on the optically transparent substrate to have its cross-sectional area imaged. The cross-sectional area is generally perpendicular to an axis that is parallel to the walls of the tube, where the axis passes through the center of the cross-sectional area. It is desirable, but not necessary for the tube to be arranged so that its center is concentric with the center of the camera 106 and the center of the source of illumination 108. In one embodiment, the tube is arranged so that the center of the cross-sectional area to be imaged lies on a single axis that includes the center of the camera 106 and the geometric center of the source of illumination 108. Upon mounting the tube 104 on the substrate with its cross-sectional area contacting the optically transparent substrate, an image of the cross-sectional area is taken by the camera and transmitted to the microprocessor, where it undergoes further processing as detailed below.

Following the capturing of the image of one end of the tube, a second image of the opposing end of the tube may be taken. When both ends of the first section are imaged, images of the second section may be captured, followed by images of the third section, and so on. A linear section of the tube is also cut and disposed upon the transparent substrate 102 and its cross-sectional properties are measured. In this manner, several cross-sectional area images of a linear tube or of a bent tube may be captured and transmitted to the microprocessor for additional computational processing. This additional processing is detailed below.

The cross-sectional image obtained by the camera 106 is divided (at both the inner diameter and the outer diameter) into a number of radial segments. The inner diameter and the outer diameter of the cross-section of the tube 104 are measured at each of these segments. In one embodiment, the cross-sectional image is divided from 2 to 288 radial segments, specifically from 24 to 144 radial segments, and more specifically from 48 to 96 radial segments. In an exemplary embodiment, the cross-sectional image is divided into 72 radial segments along both the inner diameter and the outer diameter. In one embodiment, the image is divided into a plurality of points not a plurality of segments. Analysis of the data is then performed on the plurality of points.

The library in the microprocessor facilitates a computation of the average inner diameter and the average outer diameter for the cross-sectional image. It also calculates the center of mas, out of roundness for the inner diameter and the outer diameter of the cross-sectional image and the resulting wall thickness across the entire cross-sectional area. The microprocessor can also calculate and locate the area of flow within the inner diameter of the tube. It can also be used to calculate and locate the presence of any flat spots present on the inner surface area of the tube.

These computations can be made for multiple standards. In one embodiment, the computations can be made for ASME B31.1-2010 and EN 2 952-5.

The values calculated for the center of mass, the inner diameter, the outer diameter, the out of roundness, the wall thickness, area of flow, length and area of the maximum flat spot in the tube wall after bending, and the like are transmitted by the microprocessor to the computer database, where they are stored. Software programs stored on the computer database are used to calculate other statistical parameters of the tube (e.g., the radius of the bend, the fluid flow area, fluid flow volume, and the like).

In one embodiment, the database is operative to facilitate a comparison between the data obtained on the bent tube and that obtained on the linear portion of the tube. The computer monitor can be used for displaying the image and calculated measurements for operator approval before performing any boiler code calculations. The system also permits the operator to select which boiler code the bent tube is expected to comply with. The system (i.e., the computer along with the associated database) permits performing calculations desired by any boiler code (including. but not limited to ASME B31.1-2010 or EN 2 952-5). The system is operative to compare the results of the boiler code calculations to the code limits to determine if each bent tube section passes or fails the code requirements.

Assessments are performed based on specified limits—minima or maxima, depending on the parameter—for various parameters. These may be either percent change from a nominal value or in measured units (either inches or millimeters). The assessments and thresholds are defined in the design codes, shop procedures, and customer requirements. The design codes define the "absolute" limits; however, specific job or customer limits may be more stringent than the design code limits.

The system 100 has a number of advantages. For example, a single enclosure can house all the equipment of the system 100. The enclosure can be bolted to a bench-top for stability and security. A small touch screen monitor (camera screen) provides for triggering inspections and viewing camera image data. A panel computer with a large touch screen monitor (main screen) provides annotation, analysis, quality record generation and storage. Network connectivity provides external access to data and records. An exemplary enclosure is about 40 inches high, 20 inches wide and 24 inches deep.

The system stores camera images, data and annotations. Results are preserved in a quality records database.

The procedure for an operator that operates the system 100 is as follows. A bend is cut into a plurality of segments as detailed above. Each segment is ground to remove burrs and sharp edges. Inspection and measurement of the segments of the bend are guided by instructions on the monitor of the system 100. A user screen on the large touch screen monitor (main screen) provides directions to place the first bent section on the optically transparent substrate. The camera is operated to capture an image of the cross-sectional area of the tube section. The camera library then uses the image as described above (e.g., dividing the image into sections) to capture the inner diameter, the outer diameter, the wail thickness, thin spots, out of roundness, flow area and area loss and provides a pass/fail assessment along with statistics (e.g., average, minimum and maximum for various parameters). The screen also permits annotation of the image and identification of the sample whose image is seen on the screen.

When the bend section is placed on the optically transparent substrate, an image of the cross-sectional area with respect to an image of the illuminating ring (the source of illumination) appears on the monitor. This image is not shown here. It is desirable for the image of the cross-sectional area of the bent tube to lie proximately close to the center of the image of the illuminating ring. The monitor thus provides positioning information (for the bent tube) to the user. For example, when the cross-section of the bent tube is not properly placed, the monitor provides an indication to the user and may not indulge in further processing of the image. On the other hand, when the cross-section of the tube is properly placed, the monitor provides an appropriate indication to the user and will proceed to further process the image.

After the image is obtained and processed (i.e., diameters are measured, center of mass is calculated, and the like), portions of the image can be annotated by the user or will automatically be annotated by the computer. In one example, sampling points across the cross-sectional area can be identified on the image. In another example, deviant wall thicknesses can be identified using colored markings on the monitor screen.

The monitor also directs the operator to remove the first bent section and replace it with the second bent section of the bent tube. The procedure above is repeated with the monitor directing the operator to perform each step along the way. In a similar manner, segments from other bend sections can be measured and characterized.

When the bent sections have been measured, the operator chooses a "switch view" operand on the screen and the screen prompts the operator to measure the properties of unbent tubes. The images are processed as detailed above. The unbent portion of the tube sample is used for comparing against the bent tube samples to check for wall thickening, thinning, area loss, and other dimensional characteristics and changes. Measurements of a straight unbent tube may be made before or after the tube is bent. The system is thus able to measure and to assess distortions due to the bending process. It can also issue pass/fail information to the user. The data is saved to the database for further compiling and for sharing with other users across the internet.

Thus, in summary, for each bend section, the system (via the monitor screen) directs the operator to first place cross-sectional area of the bend on the optically transparent substrate. The system obtains a first image and processes this image. Following this, the system directs the operator to place an unbent cross-sectional area on the screen. The system obtains a first image and processes this image. Dimensions obtained from the two images are compared to obtain pass/fail information. The data can be reviewed by the operator and stored on the data base, printed out onto a sheet of paper or a compact disc to provide a hard copy, following which the next bend section can be examined. In this manner, a plurality of bend sections can be rapidly characterized.

In one embodiment, the system is operative to combine the calculated results from multiple tube cross-sections into an overall calculation for boiler code compliance for linear tubes or for bent tubes. The computer monitor permits the display and compiling of images of each tube cross-section, annotated with measurements and locations, into the inspection report. The computer database is operative to save all key measured and calculated data and this data can be stored, manipulated or summarized into a quality records database. The database can be used to generate an inspection report at any desired time and the contents of this report can be adapted depending on the requirements of the boiler code selected by the operator. The database is operative to provide the inspection report in a variety of different languages on command (examples being English, German, and Chinese languages). The inspection report can be generated in a variety of different formats (e.g., PDF, HTML, and the like). The computer database can also guide an operator who is not familiar with the boiler code compliance calculations through the process of taking all desired measurements and generating an inspection report.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A system for determining quality of a tube, the system comprising
   an optically transparent substrate having a first side and a second side that are opposed to each other;
   a microprocessor;
   a database;
      a camera disposed upon the first side of the optically transparent substrate;
      and a source of illumination; the source of illumination being disposed on the first side and being operative to illuminate the tube disposed on the second side of the optically transparent substrate;
         wherein the camera is in operative communication with the microprocessor and the database;
         wherein the camera is operative to capture an imago of a cross-sectional area disposed upon the second side of the optically transparent substrate;
         wherein the microprocessor is operative to calculate dimensions and geometry of the tube from the image and determine acceptance or rejection of the tube based upon a parameter; and
         wherein the source of illumination optically illuminates the cross-section of the object.

2. The system of claim 1, wherein the tube is selected from the group consisting of a linear tube and a bent tube.

3. The system of claim 1, where the optically transparent substrate is selected from the group consisting of quartz, silica, alumina, titania, polystyrene, polycarbonate, polymethylmethacrylate, polycarbonate, polyester, polyetherimide, and a combination thereof.

4. The system of claim 1, wherein the source of illumination comprises a plurality of point sources of light arranged in a ring around the camera.

5. The system of claim 1, wherein the entire system is enclosed in an opaque case with an opening for introducing and removing the tube.

6. The system of claim 2, wherein data obtained on the inner tube and data tube obtained on the bent tube are compared.

7. The system of claim 1, wherein the camera is in electrical communication with the microprocessor and the database; and wherein the electrical communication is selected from the group consisting of electrical hard wiring, wireless communication, or a combination thereof.

8. The system of claim 1, wherein the determining quality standard is in accordance with ASME B31.1-2010 or EN 2 952-5.

9. The system of claim 1, wherein the microprocessor comprises an image processing library for the tube.

10. The system of claim 1, wherein the system is operative to compute a value selected from the group consisting of an inner diameter, an outer diameter, the wall thickness, an out of roundness of the tube, an area of flow, center of mass and a size of flat spots on an inner surface of the tube.

11. The system of claim 1, wherein the system is operative to perform calculations required by a boiler code.

12. The system of claim 1, wherein the system is operative to calculate and compile results from a plurality of tube cross-sections into an overall calculation of boiler code compliance for a bent tube.

13. The system of claim 1, further comprising an opaque cover which prevents external light from impinging on the system and interfering with the image.

14. The system of claim 12, wherein the system is operative to compute a value selected from the group consisting of a radius of the bend, a flow area, an average inner diameter and an average outer diameter.

15. The system of claim 1, further comprising a monitor for viewing camera image data or triggering inspections.

16. The system of claim 1, further comprising a user display for displaying images of the tube located on the optically transparent substrate, annotating the image or locate the tube properly on the optically transparent substrate.

* * * * *